(12) United States Patent
Valencia

(10) Patent No.: US 8,993,482 B2
(45) Date of Patent: Mar. 31, 2015

(54) PROCESS TO MAKE PELLETIZED GRANULES BASED ON ENDOMYCORRHIZAL FUNGI COVERED WITH MINERALS CLAYS AND THEIR COMPOSITION

(76) Inventor: José Luis Miranda Valencia, Celaya (MX)

( * ) Notice: Subject to any disclaimer, the term of this patent is extended or adjusted under 35 U.S.C. 154(b) by 0 days.

(21) Appl. No.: 13/581,280

(22) PCT Filed: Oct. 25, 2010

(86) PCT No.: PCT/MX2010/000116
§ 371 (c)(1),
(2), (4) Date: Nov. 11, 2012

(87) PCT Pub. No.: WO2012/047081
PCT Pub. Date: Apr. 12, 2012

(65) Prior Publication Data
US 2013/0196850 A1    Aug. 1, 2013

(30) Foreign Application Priority Data
Oct. 4, 2010 (MX) .................... MX/a/2010/010894

(51) Int. Cl.
| *A01N 65/00* | (2009.01) |
| *A01N 63/04* | (2006.01) |
| *C05F 11/08* | (2006.01) |
| *C05G 3/00* | (2006.01) |

(52) U.S. Cl.
CPC ................ *A01N 65/00* (2013.01); *A01N 63/04* (2013.01); *C05F 11/08* (2013.01); *C05G 3/0047* (2013.01)
USPC ......................................................... 504/117

(58) Field of Classification Search
None
See application file for complete search history.

(56) References Cited

U.S. PATENT DOCUMENTS

| 4,316,813 A * | 2/1982 | Voss ............................... 252/189 |
| 2008/0064598 A1 | 3/2008 | De Rougemont et al. |

FOREIGN PATENT DOCUMENTS

| CA | 1270454 | 6/1990 |
| EP | 314439 A2 * | 5/1989 |
| EP | 0485229 | 1/1995 |

OTHER PUBLICATIONS

Lynch, "Limits to microbial growth in soil" Journal of General Microbiology (1982), vol. 128, pp. 405-410.*
"Silt", Merriam-Webster [online], downloaded (Jul. 19, 2013) from URL <http://www.merriam-webster.com/dictionary/silt>.*
Merriam-Webster Dictionary definition on "Silt"; 3 pages, Jul. 16, 2013.
Lynch; "Limits to Microbial Growth in Soil"; Journal of General Microbiology (1982) vol. 128, pp. 405-410.
Hall; "Soil pellets to introduce vesicular-arbuscular mycorrihizal fungi into soil"; Soil Biology and Biochemistry (1979) vol. 11. No. 1; pp. 85-86.

* cited by examiner

*Primary Examiner* — Abigail Fisher
*Assistant Examiner* — Daniel L Branson
(74) *Attorney, Agent, or Firm* — Thorpe North & Western, LLP

(57) ABSTRACT

The present invention relates to a composition of granulated or pelletized endomycorrhizal fungi spores coated with a covering of mineral clays and binders with calcium sulphate monohydrate and the production and use thereof in agriculture.

13 Claims, 2 Drawing Sheets

PROCESS TO MAKE PELLETIZED GRANULES BASED ON ENDOMYCORRHIZAL FUNGI COVERED WITH MINERALS CLAYS AND THEIR COMPOSITION

FIELD OF THE INVENTION

The present invention relates to a process to obtain a composition in the form of pelletized granules with spores of endomycorrhizal fungi covered with mineral clays and the composition thus obtained. The process of covering and pelletization in granulated form of spores of at least one species of endomycorrhizal fungi by its incorporation to minerals clays mixture comprising motmorillonites, kaolinites and bentonites, that includes basically 3 stages: mixing, pelletization and drying; this covering serves like an armor for spores of the endomhycorrizal fungi so that it protects against the adverse environmental conditions and its confers them resistance to the handling avoiding its destruction by mechanical damage that it could occur during its handling. It also protects against drastic changes of temperature avoiding its dehydration and/or death. Also it avoids the direct exposure of the microorganisms with fungicides that can destroy them and against the contamination with parasites or some injurious agents. Besides the benefits above described, the present invention provides a product of easy and practical handling during its application in agriculture, alone or in mixture with the fertilizer; by its size of particle and hardness, it allows to obtain homogenous mixtures without degrading to dust, thus saving times, workforce and costs. It is an effective and highly versatile product.

BACKGROUND OF THE INVENTION

At present, diverse processes are known to obtain products with spores of mycorrhizal fungi, for example, that described in document DE3932746 (A1). This document describes a material of support with dibasic mineral wool for the production and application of vesicular-arbuscular mycorrhizal fungi. This material of support has many advantages in comparison with the expanded clay, but this document does not mention nor anticipates the process described in the present invention. In addition the composition in the form of pelletized granules with spores of endomycorrhizal fungi covered with mineral clays of the present invention is not mentioned nor suggested. In addition, CA 1270454 (A1), describes a process to prepare a composition of inoculant support to inoculate a plant of vesicular-arbuscular mycorrhizal fungi, the process comprise to deal an adsorbent particle with internal surfaces greater than the outer surfaces, with roots of the plant infected with vesicular-arbuscular mycorrhizal fungi during at least two weeks to give a yield by roots that contain adsorbent particles in association with the fungi. The porous material is selected of expanded clay, pumice stone and polystyrene, in addition the adsorbent particles include an inflatable material of secondary clay, in combination with more of 50% in weight of a diluent and in combination with more of 50% in weight of sand, earth or humus, but this document does not mention nor anticipates the process and the composition described in the present invention. In the document U.S. 2008/0064598 A1, it described preparations of mycorrhizal fungi that form arbuscules, to obtain these preparations an inoculant is cultivated in porous granulating and the crude inoculant that is produced is ground in such a way that active spores are not destroyed. Porous granules as substrate are of expanded clay or atapulgite or expanded slate or volcanic rock or pearlite or vermiculite or mixtures of two or more of these materials, but this document either mentions and neither anticipates the process and composition described in the present invention. The present invention is considered by the inventors to be new and inventive and is not suggested or anticipated by documents before mentioned.

In order to study mineral particles of a ground, the scientists classify them regulating in advisable groups according to its size. These different groups are called fractions, separatas or separated. The analytical procedure by which the particles are thus separated calls mechanical or grain sized analysis. It is really a determination of the distribution of the particle sizes. According to the System of the Department of Agriculture of the United States and the International System of the Sciences of the Ground, the classification of grounds is mentioned in the following way (Table 1):

TABLE 1

Classification of particles of the ground according to two systems (U.S.A and International)

| Fraction of the ground | System of the Department of Agriculture of the United States[a] Diameters limits in mm | International System of the Science of the ground[b] Diameters limits in mm |
| --- | --- | --- |
| Very heavy sand | 2.00-1.00 | |
| Heavy sand | 1.00-0.50 | 2.00-0.20 |
| Medium sand | 0.50-0.25 | |
| Fine sand | 0.25-0.10 | 0.20-0.02 |
| Very fine sand | 0.10-0.05 | 0.02-0.002 |
| Slimes | 0.05-0.002 | |
| Clay | Less than 0.002 | Less than 0.002 |

So that a ground is to be designated as a clay it must have, like minimum, a 35% of argillaceous fraction. The clay exists in the call colloidal state, in which their individual particles are characterized by their extraordinarily small size, great area of dispersion by mass unit and the presence, in surface, of electrical charges to which the water molecules feel attracted so much as ions.

The clay particles commonly are prepared in plates or grudges, like mica, and if they become damp are very plastic. When the clay with a suitable amount of water gets wet, it dilates and it becomes sticky. When it dries it shrinks with the adsorption of considerable energy. Becoming damp again, it appears the swelling, with change of temperature. The absorbent capacity of clays for water, gases and solubles salts are very high.

It recognizes three types of important minerals, although others are known in significant quantities, kaolinite, illite and montmorillonite. These groups greatly vary in plasticity, cohesion and adsorption, being the kaolinite the lowest in these properties and montmorillonite the highest.

Chemically the kaolinite and the other members of this special group are aluminic silicates. The same happens to the montmotillonita and other clays of the same type of crystallization, but these take in addition sodium, iron or magnesium, according to the cases.

A bentonite is a compound rock essentially by minerals of the group of the smectites. The criteria of classification used by the industry are based on their behavior and physic-chemical properties; thus the more accepted industrial classification establishes three types of bentonites based on its capacity of swelling in water:

Bentonite highly inflatable or sodics
Bentonites little inflatable or calcics

Bentonites moderately inflatable or intermediate.

Physic-Chemical Properties of Clays

The physic-chemical properties of clays derive, mainly of:

Its extremely small sizes of particle (inferior than 2 μm)

Its laminar morphology (filosilicates)

The isomorphic substitutions, that cause the appearance of load in laminae and to the cation presence weakly related in the interlaminar space.

As a result of these factors, they present, on the one hand, a high value of superficial area and, simultaneously, the presence of a great amount of active surface, with unsaturated bonds. For that reason they can interact with very diverse substances, in especially compounds polar, reason why they have plastic behavior in mixtures clay-water with high proportion solid-liquid.

The high plasticity of clays is consequence, again, of its laminar morphology, extremely small particle size (high superficial area) and high swelling capacity. In general so more small are the particles and more imperfect its structure, the material is more plastic.

Fertility

It recognizes six external factors that influence in the life of the plants: light, mechanical support, temperature, air, water, and nutrients. Except the light, the ground is an agent of supplying of all these factors. The capacity of grounds to supply some essential elements to the plants superiors is a fundamental problem in the production of harvests. In order to obtain that the secondary nutrients and micronutrients that are applied to the ground through use of fertilizer do not react forming compound that prevents their assimilation, it is necessary that they are in grounds where a high capacity of cationic exchange exists. This is not always possible and sometimes when they are applied they arrive in very small amounts or they absolutely do not arrive at the plant to react and to become on non assimilable compound. This brings consequently that it must use high amounts of fertilizer being few economic and for long time can get to be toxic for the ground besides causing to its eutrophycation and the contamination of water bodies.

In the last decades it has been tried to change in the global scope the paradigms of the agricultural production that implied the intensive use of energy, machinery and chemical substances, by a new concept, the one of viable agriculture. According to this new concept viable agriculture must:
 a) To satisfy the human needs of fiber and foods.
 b) To improve the environmental quality and the base of natural resources on which the agricultural economy depends.
 c) To make an efficient use of the nonrenewable resources.
 d) To maintain the economic viability of the agricultural activities and
 e) To increase the quality of life of the agriculturists and the society like a whole.

In agreement with these needs the use of biofertilizers, that is to say, products of natural occurrence, whose active ingredient are spores or vegetative cells of microorganisms, or extracts of plants; it is a useful tool to approach us to an viable agriculture.

An example of this type of product are the mycorrhizas, that are beneficial associations that settle down between some fungi of the ground and the roots of vascular plants.

The mycorrhizas improve the growth of the plant with the increase of the surface of absorption of the radicular system; with the selective absorption and with the accumulation of certain nutrients, especially phosphorus; with the solubilization and dispose some minerals normally insoluble, allowing that the nourishing roots work during more time; and causing that the nourishing roots been more resistant to the infection that cause some pathogenic fungi to the ground such as *Phytophthora*, *Pythium* and *Fusarium*.

In the literature it appears reported the tendency of the endomycorrhizal fungi to spore within others spores of endomycorrhizal fungi suggesting that dead spores provide of a favorable microhabitat for the formation of spores. Also one has reported a greater sporulation of endomycorrhizal fungi within rest of insects, dead seeds and seminal covers, which has been interpreted like a mechanism that would favor the survival of the set out spores to adverse environmental conditions. This fact has been made by some authors for the use of expanded clay in the production of commercial inoculant, since that spores proliferates within the cavities produced by clays.

At present there exist several inoculant products made with endomycorrhizal fungi like dust whose application is traditionally direct to the seed. In this type of products like dust, the endomycorrhizal fungi are totally set out to the environmental conditions and the mechanical damage during the handling of the product, suffering structural rupture or even their death, which considerably decreases the effectiveness of the product. At being exhibited the structures of the endomycorrhizal fungi exists the risk of they enter in direct contact with some product fungicide that has also been applied to the seed causing its death. Under this same context, the fungi are susceptible to be parasitized by some injurious agent preventing their installation in the root of the plants and/or causing their death. In these dust products also exists the possibility of death of the endomycorrhizal fungi by drastic and continuous changes of temperature, the spores tends to undergo dehydration. Besides the above mentioned, the use of adherents is generally rigorous so that the dust product can fix to the seed, which makes more expensive the application, this work requires of enough time and manpower. Sometimes the dust disperses in water for its application to the ground, nevertheless, this dust is not soluble in the water and far from to optimize the application it returns inefficient so that the dust settles within the application equipment and covers the holder of the seeding machines that are used, causing that the packings wear out, the adjustment of the equipment is very expensive and it loses long time and product. By the nature of these dust products, its application in mixture with granulated fertilizers would be inefficient since a good homogenization due to the difference in the particle size is not obtained.

DESCRIPTION OF THE INVENTION

The present invention relates to a process to obtain a composition in the form of pelletized granules based on spores of endomycorrizhal fungi covered with mineral clays and the composition thus obtained, as well as its use in agriculture.

It is known that when they are handled or diverse compositions with mycorrizhal fungi are applied to the ground, are degraded easily under adverse environmental conditions, are destroyed by mechanical damage during its handling, they are contaminated or they are destroyed with fungicides, parasites or some injurious agent, in addition they are delicate products and of difficult handling.

All of these problems are solved surprisingly with the procedure and composition of the present invention.

In a modality of the present invention the composition comprising:
 a) a mixture of spores of endomycorrhizal fungi and sterilized slime in a proportion of 15% up to 30% in weight;
 b) mixture of mineral clays in a proportion of 58% up to 75% in weight, and c) binder in a proportion of 10 up to 12% in weight.

The mixture of spores of endomycorrhizal fungi with sterilized slime contains a concentration of spores from 0.05% to 0.10%, this concentration allows that the final pelletized product contains up to 3,000 spores viable/kg, amount that guarantees an efficient use of the product.

This mixture comprises at least one of the following species of endomycorrhizal fungi: *Glomus fasciculatum, Glomus constrictum, Glomus tortuosum, Glomus geosporum, Glomus intraradices*, and/or mixtures of these.

In this composition the selection of the components in theses percentage has a surprising effect, that is to say the mixture of clays montmorillonite, kaolinite and bentonite covers to spores of endomycorrhizal fungi, this mixture of clays can be in a proportion:

Montmorillonite from 0.3 to 0.7
Kaolinite from 0.3 to 0.7
Bentonite from 0.5 to 1.2

In one preferred embodiment, the composition of mixture of mineral clays montmorillonite, kaolinite and bentonite is of 0.5:0.5:1.

In agreement with the antecedents, the size of particle of the components of the mixture plays an important role to obtain a suitable homogenization and formation of granules. The mixture of sterilized slime with spores of endomycorrhizal fungi must contain particles whose size are mesh 40 (0.425 mm) or less. Of same way, the size of particle of the components of the mixture of clays are between mesh 80 (0.180 mm) and mesh 100 (0.150 mm).

Another embodiment of the invention consists of the process to obtain a mineral composition based on spores and mineral clays for its use in the agriculture that includes the following stages:

i) The mixture of clays is introduced in a mixer hopper along with the sterilized slime that contains spores of the endomycorrhizal fungi and the binder, in this first stage it carries out a mixture in dry of all the ingredients. In this point the clays make contact with spores of the mycorrhizal fungi and begin the cover process. The use of a binder is essential to confer to the granule a greater hardness. This mixture maintains the components in the proportions and ranks described previously until its complete homogenization.

ii) Once passed the necessary time until obtaining a homogenous mixture, this one is spilled in a pelletized plate to a flow from 15 to 20 kg/min. The plate has a diameter between 1.5 and 2.5 m, with a rake angle of 25° to 45° and turns from 5 to 20 rpm. Water is sprinkled on the mixture in the plate to a flow from 1 to 2 L/min to begin to form granules. In this point spores are completely immersed and covered by clays.

iii) The formed granules are fed to a rotatory furnace of 3 sections, warmed up by a burner that is fed with a mixture of hydrocarbons predominating the methane. In its interior the furnace reaches a temperature of 400° to 500° C. in the first section, in the second section the temperature is reduced to a rank between 200 to 300° C. and in the last section the rank of temperatures decrease up to 80 and 130° C.

iv) Finally, the obtained granules are passing through a system of sieves where the mesh of greater opening is number 3 (5 mm) and the smallest number 20 (0.85 mm). The product that is retained between these meshes is the suitable one and it is come to package in coats or bags of paper. This is made with the purpose of to guarantee that the product that will be given fulfills the conditions of optimal granulometry for its easy application.

One more embodiment of the invention consists of that the mixture of the components subject to the process previously described eliminates the water of the final pelletized product to be able to obtain a low humidity concentration between 2% and 6%, which allows that it can also be mixed with hygroscopic fertilizers like the urea, without problems that can affect their physical characteristics.

Still more, another embodiment of the invention comprises or consists of the binder use in the mixture to obtain the granulated product. There were realized different tests with different binder like: hydrous lime, molasse, pectin, sulphonate of calcium and sulphate of calcium monohydrated; and in agreement with the obtained results the binder with better results is the sulphate of calcium monohydrated.

In addition, another embodiment of the invention comprises or consists of which the use of the binder confers to the dried granulated product properties of suitable hardness that will give resistance against mechanical damages by handling and storage. The dried granulated product presents hardness between 1.9 to 2.3 $kg/cm^2$ this hardness is measured with penetrameter or hardometer.

Another objective of the present invention is the agricultural application of mycorrhizas. The product granulated elaborated with spores of endomycorrhizal fungi that are covered by a mineral clay mixture (montmorillonites, kaolinites and bentonites) to which makes reference the present invention, is a versatile product of easy and practical application. Its presentation is in granulated form, with a size of particle among 0.85 to 5.0 millimeters, appropriate size that allows it to be easily applied alone or in mixture with other fertilizers. It account with hardness between 1.9 to 2.3 $kg/cm^2$, sufficient to support the handling during the preparation of the product and later in the mixed with other fertilizers. To be mixed with other fertilizers it has a low degradation to dust and has in addition the capacity to be 100% disgregable, dissolved, or dispersed in water, a characteristic that allows it to arrive at the roots of the plants. Thanks to these characteristics its application becomes simple and practical, saving times, manpower and costs. In addition, as already it were mentioned, spores of the endomycorrizhal fungi is covered by a mineral clays mixture (montmorillonites, kaolinites and bentonites) and later is put under a pelletization process (granulation), it protects them against the mechanical damage that could be present during the handling of the product doing more effective each application. Spores are also protected against drastic changes of temperature, or against the infection of some parasite or the contamination of some injurious agent, avoiding their destruction and/or death. This granulated product can be only applied alone or in mixture with fertilizers direct to the ground, as it is not applied to the seed, it is not necessary the use of any adherent either of any class of additive class or carriers.

EXAMPLES

The following examples have the purpose of illustrating the invention not to limit it, any variation or valuation by an expert in the technique will fall in the scope of the present invention.

Example 1

In order to produce one ton of this granulated composition 150 kg of a composed mixture are introduced in mixer by 0.05% of spores of endomycorrhizal fungi and 99.5% of sterilized slime, 730 kg of mixture of clays montmorillonites, kaolinitics and bentonitics pulverized, and 120 kg of binder of sulphate of calcium monohydrated; all is mixed until obtain a homogenous mixture. The mixture is emptied in a pelletized plate where water is sprinkled on the mixture to form granules to a flow of 1.25 L/min. The formed granules are fed to a rotatory furnace of three sections with a profile of temperatures of 450, 225 and 100° C. to each one of the sections and to obtain a final humidity of the product of 5%. After the drying, the granules are sieved through mesh of opening 0.85 mm (mesh 20) and 5.0 mm (mesh 3). A product granulated with a hardness of 2.0 kg cm$^2$ was obtained.

The granulated product that is obtained can be applied in dose of 10-30 kg/ha in any growing, alone or in mixture with the fertilizer, grounds where the established growings are with low levels of fertility.

Example 2

A process for the selection of temperatures was carried out to which the granulation process will be realised. For it 4 temperatures were chosen to which the furnace operates. These temperatures were selected in function of the drying processes on which already it was counted for the drying of other products based on mineral clays. The chosen temperatures for the experimentation were: 300, 500, 600 and 900° C. The answer of evaluated exit was the viability of the product expressed in number of spores viable/kg of sample.

The results are showed in the graph of FIG. 1. Where it is observed that, the viability decreases as the temperature of drying is increased. The greater viability is obtained with the minimum temperature, nevertheless, the humidity of the granule is very high and causes that the granule be dispersed. The ideal conditions were determined in the point where it is not affected of drastic way the viability of spores either the humidity of the product.

In order to evaluate the viability of spores the following protocol was followed:

1.—To weight the sample: 20 grams of granulated sample are weighed.

2.—Analysis of the sample: They were analyzed by method of sieved and centrifuged in gradients of saccharose. They are taken between 10 to 100 g of sample.

a) To sieve: The sample goes through three sieves of downward diameter (10, 170, 200) They are rinsed with water by about 10 to 20 min. When it is realized this step is due to have well-taken care of to avoid splashes or losses of product.

b) To weight: The sample is weighted that remained in last two sieves and it placed from 1 to 3 g in a tube of centrifuge (of 50 ml), is added of 10 to 20 ml of water and with a syringe 20 ml of saccharose solution at 72% and Tween 80 at 2%, so that the solution is below the material suspended in water.

c) Centrifuged: The tubes are balanced and centrifuged during 5 min at 2000 rpm. The tubes are removed from the centrifuge taking care of not breaking the interface water-saccharose.

d) Observation: With the aid of a syringe, one crosses all the surface of the interface and a little of this to gather spores that did not cross the solution. It is placed in the smallest sieve to wash and to clear the excess of saccharose. They reclaim in a paper filter for its later observation in stereoscopy. Once separated the mycorrhizas, are realised assemblies in microscope to evaluate their morphologic state, and to evaluate if they can be considered like viable or nonviable according to the following criterions: Turgot and color, to do considering of viability, as showed in the FIG. 2.

In this figure also the separation of spores is observed, in addition in FIG. 2. *a*) Spore considered viable with characteristic color and turgot, in FIG. 2. *b*) Spore considered died by the color that it presents and without turgot and FIG. 2. *c*) Spore considered nonviable by breaking of cell wall.

Example 3

The effect of the product granulated with spores of endomycorrhizal fungi in wheat plants was evaluated. Plants were seeded in flowerpots with granulated mycorrhizas and other plants with granules of clay without mycorrhizas.

At first the counts of spores contained in the applied dose to fit the concentration by flowerpot were realised, in such a way that the concentration of 30 000 spores/hectare was fulfilled.

Throughout the vegetative growth the results became evident that show that the treatments with product granulated based on spores of endomycorrhizal fungi are recommendable options as complement in the nutrimental handling of the cycle of the plants (in this case the wheat). The application of such treatments results in greater vegetative development and greater aptitude of the radicular zone to absorb nutrients.

DESCRIPTION OF THE DRAWINGS

FIG. 2 *a*), represents one spore considered viable with characteristic color and turgot in one embodiment of the present invention.

FIG. 2 *b*) represents one spore considered died by the color that it presents and without turgot in one embodiment of the present invention.

FIG. 2 *c*) represents one spore considered nonviable by breaking of cell wall in one embodiment of the present invention.

Figure 1:
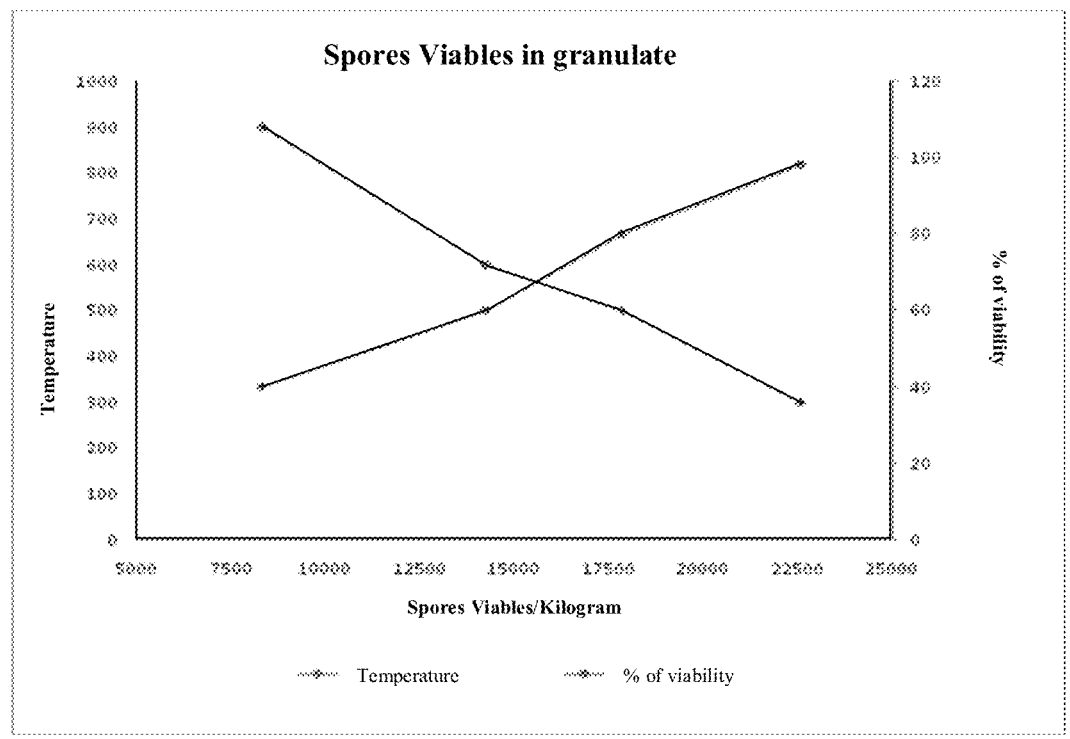
FIG. 1, is a graph that represents the evaluation of temperature of drying versus viability of spores, expressed in number of spores viable/kilogram where it is observed that the viability decreases as the temperature of drying is increased in one embodiment of the present invention.
Figure 2:
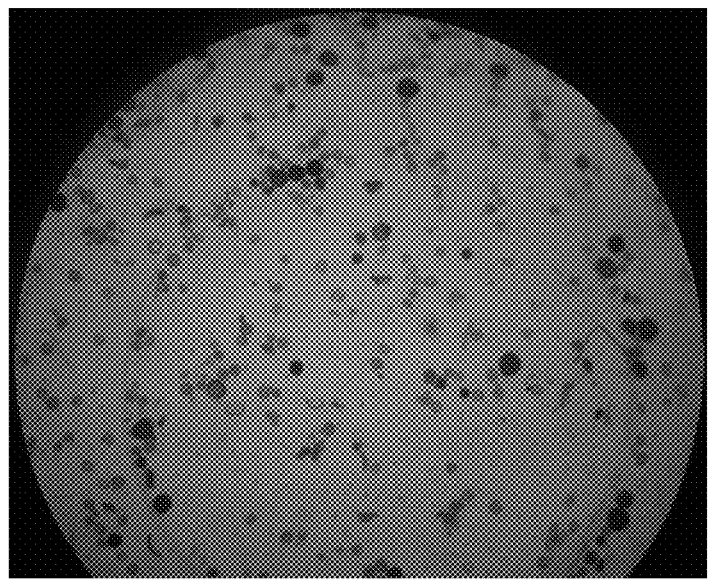
FIG. 2, represent a photography of the separation of spores in one embodiment of the present invention.
Figure 2:
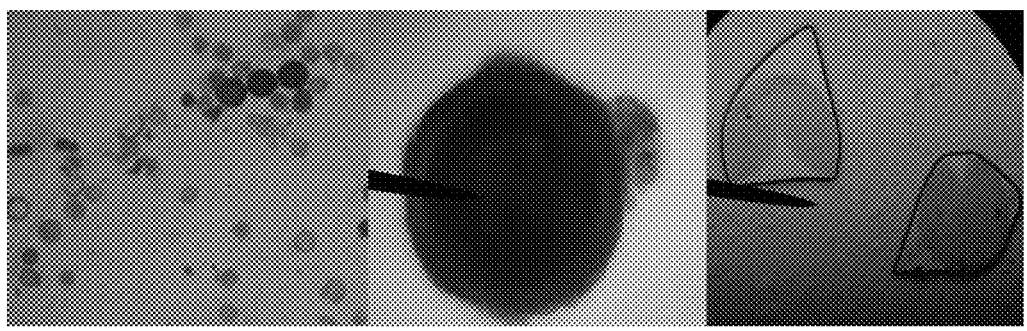

It is pointed out that in relation to this date, the best method known by the applicant to take to the practice the mentioned invention, is the one that is clear from the present description of the invention. However, it is to be understood that the scope of the present claims is not to be limited thereby.

The invention claimed is:

1. A composition in the form of pelletized granules based on spores and mineral clays for its use in agriculture comprising:
   a) a mixture of spores of endomycorrhizal fungi and a sterilized slime in an amount of between 15% and 30% in weight of the composition;
   b) mixture of mineral clays in a proportion of between 58% and 75% in weight of the composition, wherein the mixture of mineral clays includes montmorillonite, kaolinite, and bentonite in a proportion of: Montmorillonite from 0.3 to 0.7, Kaolinite from 0.3 to 0.7, Bentonite from 0.5 to 1.2; and
   c) a binder in a proportion of between 10 and 12% in weight of the composition, wherein the binder is a sulphate of calcium monohydrated.

2. A composition according to claim 1, wherein the spores of endomycorrhizal fungi are selected from the group consisting of at least one of the following species of endomycorrizal fungi: *Glomus fasciculatum, Glomus constrictum, Glomus tortuosum, Glomus geosporum* and *Glomus intraradices* and mixtures thereof.

3. A composition according to claim 1, wherein the mixture of the slime and spores of endomycorrhizal fungi has a concentration of spores between 0.05 and 0.10% in weight of the composition, which allows a final pelletized product to contain up to 3,000 viable spores per kg of product thus guaranteeing an efficient use of the product.

4. A composition according to claim 1, wherein the granulometry of the mixture of slime and spores of endomycorrhizal fungi is 0.425 mm (mesh 40) or less.

5. A composition according to claim 1, wherein the granulometry of the clay mixture is between 0.180 mm (mesh 80) and 0.150 mm (mesh 100).

6. A composition according to claim 1, wherein the use of sulphate of calcium monohydrated as a binder is confers to the pelletized product a hardness of between 1.9 and 2.3 kg/cm2.

7. A composition according to claim 1, wherein the mixture of clays of montmorillonite, kaolinite and bentonite covers the spores of endomycrorrhizal fungi in a manner sufficient to protect them against adverse environmental conditions, mechanical damage during its handling, drastic changes of temperature, dehydration, and avoids contamination from parasites or other injurious agents.

8. A composition according to claim 1, wherein the granulated composition can be used alone or in a mixture in homogenous form with other granulated fertilizers.

9. A process to obtain a composition in accordance with claim 1, comprising the steps of:
   i) mixing in dry form;
      a) a proportion of endomycorrizhal fungi spores and a sterilized slime in a proportion of between 15% and 30% in weight of the composition;
      b) a mineral clay mixture in a proportion of between 58% and 75% in weight of the composition, and
      c) a binder in a proportion of between 10% and 12% in weight, until the mixture is homogenous;
   ii) pelletizing the homogenous mixture to form granules of the homogenous mixture using a pelletized plate in a flow of from 15 to 20 kg/min, the plate having a diameter between 1.5 and 2.5 m, with a rake of 25° to 45° and which turns from 5 to 20 rpm, while sprinkling water on the mixture in the plate to a flow from 1 to 2 L/min to begin to form grains;
   iii) drying the granules using a rotatory furnace of 3 sections, the furnace reaching a temperature of 400 to 500° C. in the first section, in the second section the temperature maintaining between 200 to 300° C., in the third section the temperature maintained between 80 to 130° C.; and
   iv) sifting the dried granules through a system of sieves having a range of openings of from number 3 mesh (5 mm) to number 20 mesh (0.85 mm).

10. A process according to claim 9, wherein in step iii) the formed granules have a low humidity concentration between 2% up to 6%, which allows the granules to be mixed with hygroscopic fertilizers without causing any problems that affect their physical characteristics.

11. A process according to claim 9, wherein in step ii) the montmorillonite, kaolinite and bentonite clay mixture covers the spores of the endomycorrhizal fungi in a manner sufficient to protect them from adverse environmental conditions, mechanical damage during its handling, drastic changes of temperature, dehydration, and contamination with parasites or other injurious agent.

12. A process according to claim 9, wherein the granulated product formed has a particle size between 0.85 mm (mesh 20) and 5 mm (mesh 3) and a hardness between 1.9 to 2.3 kg/cm2.

13. A pelletized granule based on spores and mineral clays for its use in agriculture formed by a composition in accordance with claim 1, wherein the granule has up to 3,000 viables spores/kg, with a size of particles between 0.85 mm (mesh 20) and 5 mm (mesh 3), a hardness between 1.9 to 2.3 $kg/cm^2$ and a low concentration of humidity between 2% up to 6%.

* * * * *